United States Patent [19]

Leysieffer et al.

[11] Patent Number: 5,776,144
[45] Date of Patent: Jul. 7, 1998

[54] DEVICE FOR POSITIONING AND FIXING OF THERAPEUTIC, SURGICAL, OR DIAGNOSTIC INSTRUMENTS

[75] Inventors: Hans Leysieffer, Taufkirchen; Rolf Lehner, Esslingen, both of Germany

[73] Assignee: IMPLEX GmbH Spezialhorgerate, Ismaning, Germany

[21] Appl. No.: 726,494

[22] Filed: Oct. 7, 1996

[30] Foreign Application Priority Data

May 10, 1996 [DE] Germany .................. 196 18 945.4

[51] Int. Cl.⁶ .................................................. A61B 19/00
[52] U.S. Cl. ........................... 606/130; 600/25; 128/746
[58] Field of Search ........................... 606/130, 109, 606/129; 128/746, 739; 600/25

[56] References Cited

U.S. PATENT DOCUMENTS

| | | | |
|---|---|---|---|
| 2,415,310 | 2/1947 | Summerville et al. | 128/746 |
| 3,196,875 | 7/1965 | Pfeiffer | 606/130 |
| 4,025,733 | 5/1977 | Klar et al. | 128/746 |
| 4,256,112 | 3/1981 | Kopf et al. | 606/130 |
| 4,638,799 | 1/1987 | Moore | 606/130 |
| 5,004,457 | 4/1991 | Wyatt et al. | 604/158 |
| 5,119,817 | 6/1992 | Allen | 606/130 |
| 5,171,240 | 12/1992 | Hanwong | 606/109 |
| 5,197,332 | 3/1993 | Shennib | 128/746 |
| 5,201,742 | 4/1993 | Hasson . | |
| 5,263,956 | 11/1993 | Nobles . | |
| 5,387,220 | 2/1995 | Pisharodi | 606/130 |
| 5,519,278 | 5/1996 | Kahn et al. | 310/326 |

FOREIGN PATENT DOCUMENTS

WO 95/22297  8/1995  WIPO .

Primary Examiner—Robert A. Hafer
Assistant Examiner—Justine R. Yu
Attorney, Agent, or Firm—Sixbey, Friedman, Leedom & Ferguson; David S. Safran

[57] ABSTRACT

Temporarily fixable positioning system (1) for secure, play-free fastening to the human body, preferably to the human skull has a base (4), a clampable ball-and-socket joint (3), a linear axis mechanism (2) fixed securely to it and a carriage (6) guided along the linear axis mechanism for receiving an actuator or sensor instrument (12). For intraoperative use, the positioning system is combined with a retractor (27). A head support (31) is provided for noninvasive diagnostic or therapeutic applications. The combination of the axial degree of freedom of linear axis (2) with the three rotational degrees of freedom of the ball-and-socket joint (3) allows four-axis, in situ positioning of the instrument on or in the skull, especially in the external auditory canal and an opened middle ear. The positioning system in combination with one of the holders enables precise positioning of an active end (14) of a guided instrument (12) relative to sensitive anatomical structures while avoiding risky relative movements.

18 Claims, 5 Drawing Sheets

DEVICE FOR POSITIONING AND FIXING OF THERAPEUTIC, SURGICAL, OR DIAGNOSTIC INSTRUMENTS

BACKGROUND OF THE INVENTION

Field of the Invention

The invention relates to a fixable positioning system for secure, playfree fastening to the human body. In particular, it relates to a device for noninvasive or intraoperative positioning and fixing of surgical, diagnostic or therapeutic instruments in the human body, especially to the human skull, preferably in the area of the external auditory canal and in the middle ear.

Description of Related Art

Based on the fact that, to some extent, considerable relative movements between the instruments and the target structures on the body can occur with hand-guided medical instruments, and that these relative movements are in part associated with considerable risks for the patient, it is desirable to anchor these instruments, on the one hand, securely to the body, while to be able to guide them in three dimensions within certain limits, after completed anchoring to the human body, on the other hand. Moreover, it should be possible to fix the three dimensional location between a positioned instrument and the destination on the body in order that a change in the position of the tool during subsequent surgical, therapeutic or diagnostic working steps is avoided.

Fixing of devices securely to the body for receiving and three dimensional positioning of suitable instruments, however, is complicated for a host of surgical interventions, especially on the human skull, since the human skull has only a few structures to which suitable holders can be reversibly attached. To prevent relative movements between the body of the patient and guided instruments, it is basically possible to securely mechanically join the patient and instrument.

In view of the extraordinarily small and sensitive anatomic structures in the human body, longer (more than a few seconds) hand-guided retention of the instrument position is almost impossible or requires from the physician or surgeon considerable expenditure of force and concentration. However, many surgical interventions in the body, mainly in the skull area, require targeted positioning of suitable instruments, which can be fixed for longer time intervals.

Two different head holders are already known from the prior art. The so-called Mayfield clamp is firmly anchored to the head end of the surgical table with a tripod. The patient's head is placed into the receiver secured to the table and is clamped there by means of three conical threaded arbors which press on the skull through the skin. The procedure is painful overall and can be implemented for neurosurgical interventions only with local anesthesia or general anesthesia, and for general anesthesia, generally, in-patient status in an ENT (ear, nose & throat) clinic is necessary.

The company Radionics of Wiesbaden, Germany has marketed a frame which is secured to the skull using four conical threaded arbors. This frame can be briefly worn by the patient on an ambulatory basis or if necessary can, likewise, be fixed on the operating table. The frame is used as a coordinate base for stereotactic target operations in the skull. With this known device, clamping of the skull with the metal arbors is painful and it should be done with local anesthesia.

Both of the described holders are used to preclude relative movements between the head and operating table. With tools likewise fixed securely to the table, then, the required precision between the tool and head can be established. These systems are technically complex, are tied to the operating room, and moreover, have the disadvantage that the patient must be anesthetized for clamping of the skull in the supporting device, since these holders work with relatively high compressive forces which are applied at several points.

SUMMARY OF THE INENTION

The object of the invention is to eliminate the disadvantages known from the prior art. Thus, in particular, a further object is to provide a, preferably, relatively small and light, multiaxial positioning system which can be directly attached to the skull of the patient in combination with a suitable holder, especially a portable head holder, without incorporating a larger base, for example, an operating table.

It is another object of the invention to provide a positioning system which can be attached, together with the holder selected for the application, to the head of the patient, without additional aids, simply and easily.

These objects are achieved in accordance with a preferred embodiment of the present invention by a manually operated positioning system of the initially mentioned type which can be locked in its degrees of freedom and which has the following components:

a base for secure connection of the positioning system to the holder;

a linear axis which can be manually positioned via a threaded drive;

a receiving device guided along the linear axis for a surgical, therapeutic or diagnostic instrument; and a ball-and-socket joint with several rotational degrees of freedom, which can be fixed via a clamp mechanism, which can be manually positioned, and which is located between the base and the linear axis.

The positioning system according to the invention allows any instrument to be accommodated, attached without play, or simply changed. Furthermore, the inventive system enables the physician to guide the attached instrument, precisely and free of relative movements, to structures in the human body by means of several axes.

The positioning system which is fixed securely to the body is used with its receiver for any actuator, sensor, mechanical or optical instruments as an "artificial, tremor-free hand" of the physician or surgeon, who can now position the free, active end of the instrument, by means of several precisionmechanical axes, at a destination on/in the body without significantly risky relative movements occurring.

By means of the clampable positioning system which is proposed by the invention, especially by the embodiments specified below, a host of advantages is achieved. A simple compact structure is formed from relatively few parts which, themselves, in turn, can be simply structured and built. This also ensures a high measure of hardware safety in proper use for users, patients and third parties. Also, external influences, such as tremors, changes in temperature, location and pressure, cannot adversely affect the function of the system.

If a destination on the body is approached, and accordingly, the position of the positioning system is to be maintained, a locking mechanism or automatic locking for rotational or translational axes of the system is advantageous. In particular, to prevent inadvertent independent shifting of the instrument sitting in the receiving device, the linear axis is made self-locking. In this case, a rotary knob can be provided which produces axial and selflocking movement of the linear axis when turned manually.

In order to provide for simple and prompt fixing of all three rotational degrees of freedom of the ball-and-socket joint in its current position, preferably, a clamping screw is provided, where, in addition, it can be provided that, when the ball-and-socket joint is unclamped, the current position of the rotational degree of freedom is ensured by frictional forces, and after closing of the clamp, is permanently maintained.

The construction and geometrical dimensions of the positioning system are preferably configured such that the operator always maintains an unobstructed view of the system, the instrument guided therein, the free active end of the instrument, and the working area, together with the destination in the body, regardless of whether treatment takes place with observation by the naked eye or using a microscope. In this way, treatments can be done in a manner which is more easily surveyed and simpler to the operator, and by which the risks for the patient are kept as low as possible.

Depending on the application, the positioning system can be attached to the body of the patient in one of several ways. For invasive intraoperative uses, it is joined, for example, securely to a retractor. For noninvasive therapeutic or diagnostic applications in the area of the ear, it is a fixed component of a suitable head support. By means of these holders (retractor or head support) relative movements between the instrument (sensor, actuator, surgical instrument) which is clamped firmly in the positioning system and the sometimes microscopically small target structures located in the body are minimized. Furthermore, for attaching the holder according to the invention to the skull, in surgical use, no additional surgical intervention, besides the body opening which is necessary anyway (skin or tissue incision), is necessary.

When using the positioning system with a head support for noninvasive applications, the system can be fixed securely to the skull without pain and avoiding surgical measures (tissue or skin incisions, etc.). In particular, the head support, on its working side, can be provided with a funnel-shaped retaining element for fixing in the auditory canal, in which, in this case, the free, active end of the instrument can be routed to the destination in the body through the funnel-shaped retaining element. In particular, for bilateral, painless attachment in the ear area of the skull, the head support can have a soft molded part which surrounds the external ear on the side opposite the working side. This molded part is then used as a second bearing surface for the head support; however, it can also be made as a one-sided headphone or as noise protection.

In order to provide for optimum matching of the clamping width of the head support, between the working side and the opposite side, furthermore, a threaded drive with a rotary knob can be provided, by means of which the clamping width can be continuously adjusted in a self-locking manner.

One preferred instrument for the intraoperative or noninvasive use of the positioning system according to the invention is an actuator and/or sensor instrument. In particular, it is a piezoelectromechanical hearing aid transducer for vibrational stimulation of the eardrum or auditory ossicles (malleus, incus, stapes) in the middle ear.

In order to place and position the instrument held in the positioning system precisely in the body, for example, the auditory canal, the opened mastoid antrum behind the auditory canal, an opening in the skull bone, or a skin incision over the spinal column are suitable as the body entry openings. In this way, microsurgical manipulations, for example, on the eardrum, on the auditory ossicle chain, in the inner ear, in the vestibular organ or in the tissue of the brain or spinal cord are possible. If, for example, a microsurgical optical fiber is used as the instrument, laser surgery on small tumors, microcoagulation or tissue obliteration are also possible. When an instrumentation laser is coupled, vibrations, for example, of the auditory ossicle chain or the eardrum can be measured without contact.

As was already mentioned above, according to a first preferred embodiment of the invention, the combination of the above described positioning system with a suitable retractor for intraoperative application is provided.

In doing so:

the base of the positioning system is joined mechanically securely to the retractor;

the positioning system is arranged on the retractor such that the individual controls point away from the body of the patient, in order that they can be manually operated without difficulty;

the instrument is located and fixed in the receiver of the carriage so that its free, active end points to the interior of the body to the destination on the body;

the controls of the positioning system are arranged such that the operating physician always has an unobstructed view of the instrument, its free, active end in the body, and the destination on the body;

the combination of retractor and positioning system is arranged such that, even relatively small body openings, which are surgically necessary anyway, are sufficient to guide the free active end of the instrument, even under microscopic control; and the positioning system and retractors can be cleaned and sterilized with simple procedures.

According to a second preferred embodiment of the invention, the combination of the described positioning system with a head support for noninvasive applications is provided.

In this case, the base of the positioning system is joined mechanically securely to the head support;

the positioning system is arranged on the head support such that the individual controls point away from the body of the patient, in order that they can be manually operated without difficulty;

the instrument is located in the receiver of the carriage such that its free, active end points to the interior of the body to the destination on the body;

the retaining element on the working side of the head support is designed such that it can be inserted with its outer surface conically into the auditory canal, and when the head support is closed, is firmly pressed into it;

this retaining element located on the working side of the head support has a, likewise, conical inside opening which acts as a passage for the free, active end of the instrument placed in the carriage and for the optical axis of a microscope;

the combination of head support and positioning system is arranged such that even relatively small body openings, for example, the auditory canal, are sufficient to place the free, active end of the instrument in the body, even under microscopic control;

the head support is designed such that it can be fixed securely, but painlessly and noninvasively, on the head by bilateral pressure of the retaining elements;

the head support is designed such that, by means of an actuating mechanism, the spacing of the two retaining elements can be changed by the patient himself or the physician;

the selected distance between the two retaining elements is secured by a self-locking device;

the two retaining elements are made either as an ear speculum, or the support, which is not combined with the positioning system, is made as an ear muff which is placed on the external ear, surrounds it, and in this way, cannot slip;

by using an ear muff as the steady the opposite ear can be insulated from sound if necessary; and by using a one-sided headphone as the support, if necessary, the opposite ear can be exposed to sound which corresponds to the current examination.

These and further objects, features and advantages of the present invention will become apparent from the following description when taken in connection with the accompanying drawings which shows, for purposes of illustration only, several embodiments in accordance with the present invention.

DETAILED DESCRIPTION OF THE PREFERRED EMBODIMENTS

Figure 1:
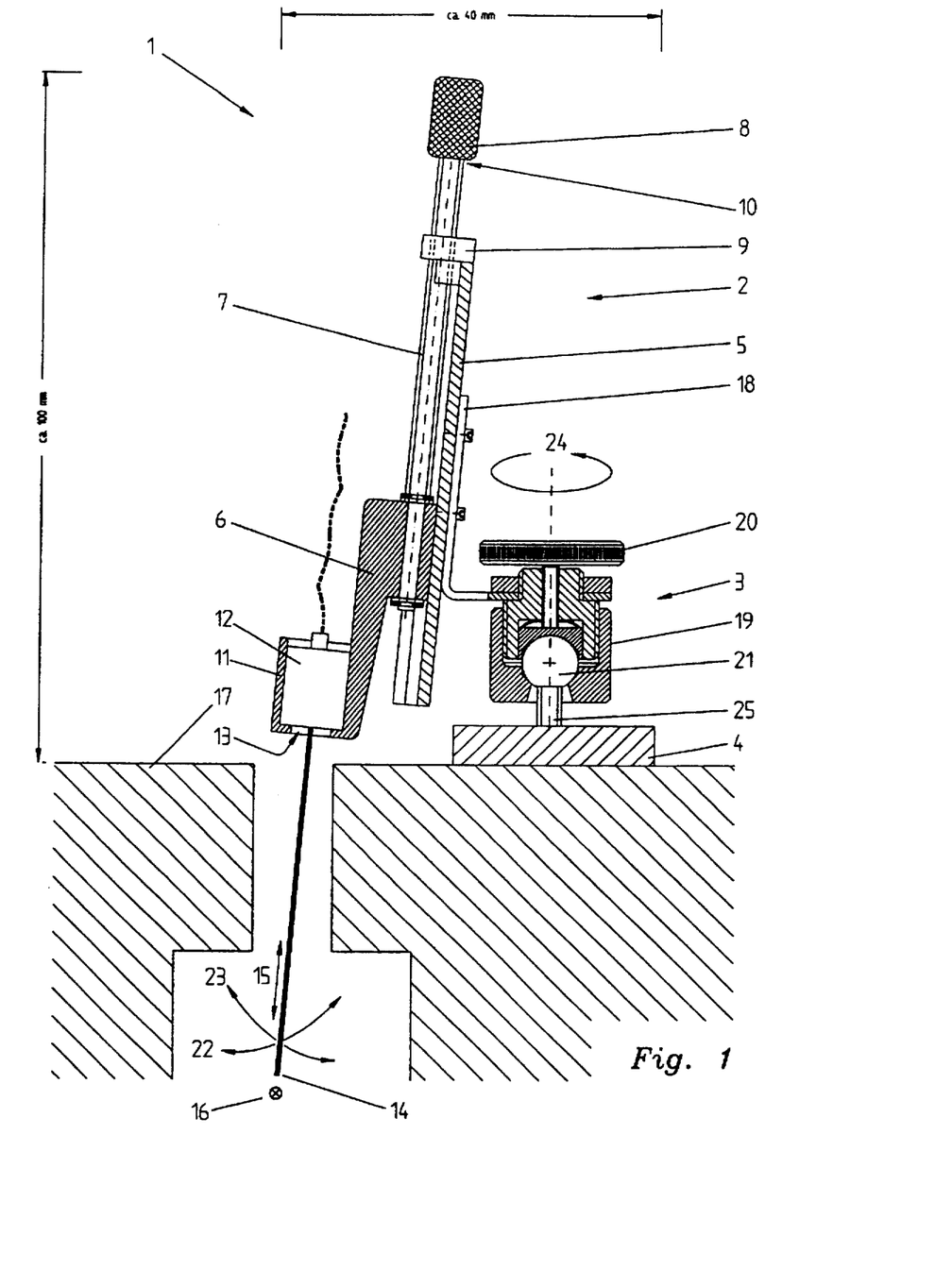
FIG. 1 shows a overall schematic view of the positioning system according to the invention.
Figure 3:
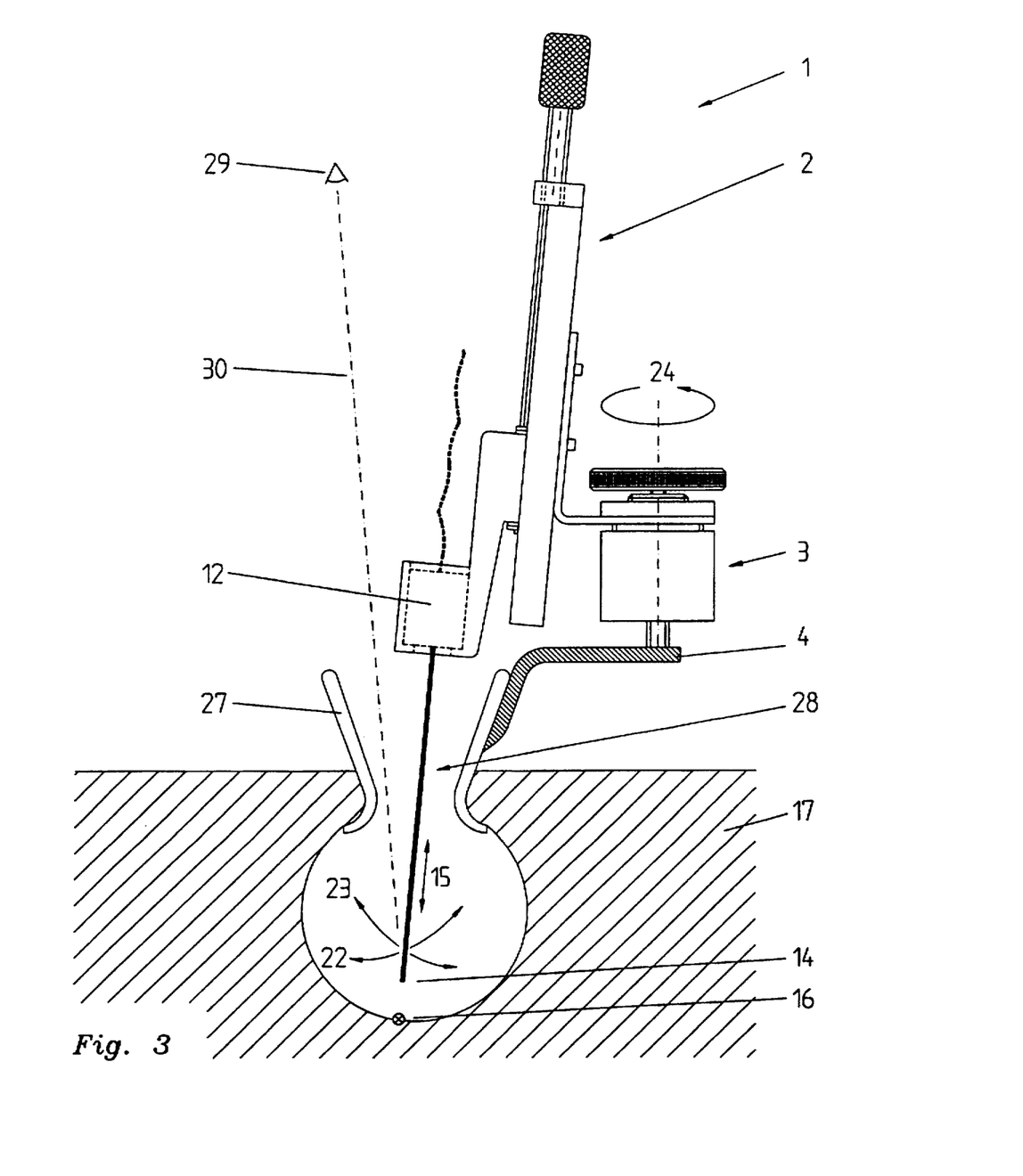
FIG. 3 shows a schematic overall view of the positioning system combined with a retractor for intraoperative use according to the invention.

The positioning system 1 shown in FIGS. 1 and 3 is composed, essentially, of a linear axis mechanism 2, a clampable ball-and-socket joint 3 and a base 4.

In linear guide 5 of linear axis mechanism 2, a carriage 6 is guided without play and it can be moved via a threaded spindle 7. A rotary knob 8 is joined securely to threaded spindle 7. The pitch of the threaded spindle 7 is designed to be self-locking, i.e. the pitch angle is smaller than the effective angle of friction, so that carriage 6 does not move automatically in linear guide 5 as a result of its weight.

Figure 1A:
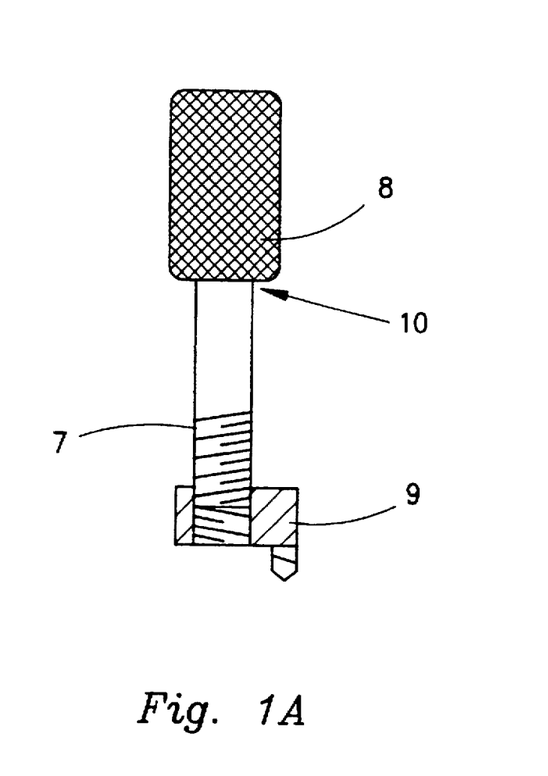
FIG. 1A is an enlarge cross-section view of a portion of the positioning system of FIG. 1 for purposes of showing the external/internal threading, respectively of the spindle and upper end stop.

The path of carriage 6 moving in linear guide 5 is limited by two end stops 9, 10. To form the upper end stop 9, a closing plate, with the corresponding internal threaded hole for threaded spindle 7, is attached to the upper end of linear guide 5. On the one hand, the closing plate forming end stop 9 guides the threaded spindle 7 parallel to linear guide 5, and on the other hand, however, also prevents carriage 6 from sliding off of linear guide 5 by screwing spindle 7 out too far.

Similarly, the end stop 10, which is used as the lower end stop on the lower end of rotary knob 8, prevents threaded spindle 7 from being screwed in too far, and thus, carriage 6 from sliding out on the opposite end of linear guide 5.

By turning rotary knob 8, according to the direction of the thread and the selected pitch of threaded spindle 7, axial displacement of the carriage 6 in guide 5 of linear axis mechanism 2 is effected. Carriage 6 can, thus, be moved continuously along the linear axis mechanism 2 between the two end stops 9 and 10, and due to the self-locking of the threaded drive, maintains its instantaneous position.

Carriage 6 has a corresponding receiver 11 into which the desired instrument 12 can be manually inserted without play or removed therefrom. Receiver 11 for instrument 12 has an opening 13 for a free, active end 14 of the instrument 12 inserted therein. The free, active end 14 of the inserted instrument 12 can, thus, be positioned parallel to the linear guide in axial direction 15 relative to destination 16 in body 17 when the rotary knob 8 is turned.

Linear axis mechanism 2, together with threaded spindle 7, rotary knob 8, carriage 6 and the instrument 12 inserted in receiver 11 and held there, is joined securely to housing 19 of the clampable ball-and-socket joint 3 using connecting element 18. Ball-and-socket joint 3 has a ball 21 which is securely joined via a column 25 to base 4, and which can be clamped with reference to the housing 19 by means of clamp screw 20.

When the ball-and-socket joint 3 is unclamped, the entire linear axis mechanism 2 can be turned in all three rotary degrees of freedom 22, 23, 24 around the center of ball 21, which is fixedly joined to the base 4.

Via base 4, positioning system 1 can be securely joined to suitable holders. After attachment of one of these holders to the body, positioning of the system attached to the holder and subsequent clamping of clamp screw 20, exact positioning of free, active end 14 without play relative to the destination 16 on the body, is thus possible, whereby possibly risky relative movements between the body and the free active end 14 of the instrument are prevented.

By loosening clamp screw 20 of ball-and-socket joint 3, connecting element 18 and the linear axis mechanism 2 which is attached to it, as well as instrument 12 inserted in carriage 6, together with its free, active end 14, can be turned around the center of ball 21 of the ball-and-socket joint 3 according to all three rotary degrees of freedom 22, 23, 24. The indicated combination of clampable ball-and-socket joint 3 and linear axis mechanism 2 attached securely to it enables, in combination, four-axis positioning of the free, active end 14 of the selected instrument 12 relative to any destination 16 on the body, i.e., in the axial direction 15 and in the three rotational degrees of freedom 22, 23 and 24.

Figure 2A:
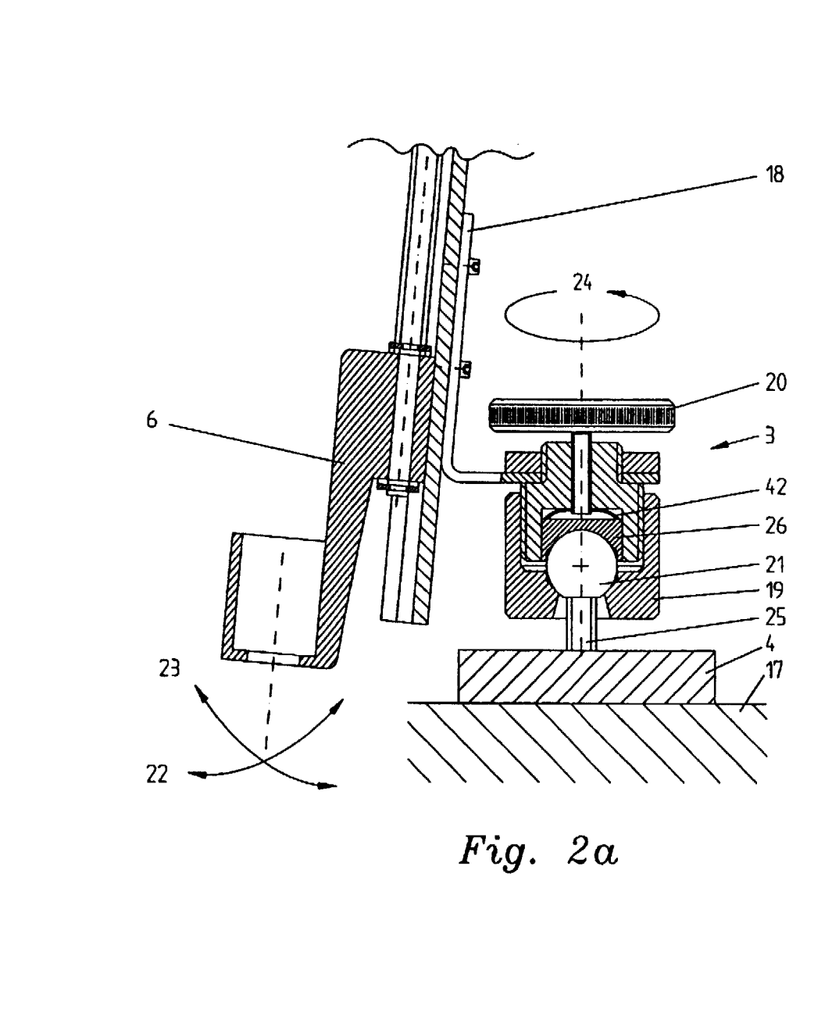
FIG. 2a shows a cutaway of the unclamped ball-and-socket joint of the positioning system according to the invention which is held by spring force in its position.
Figure 2B:
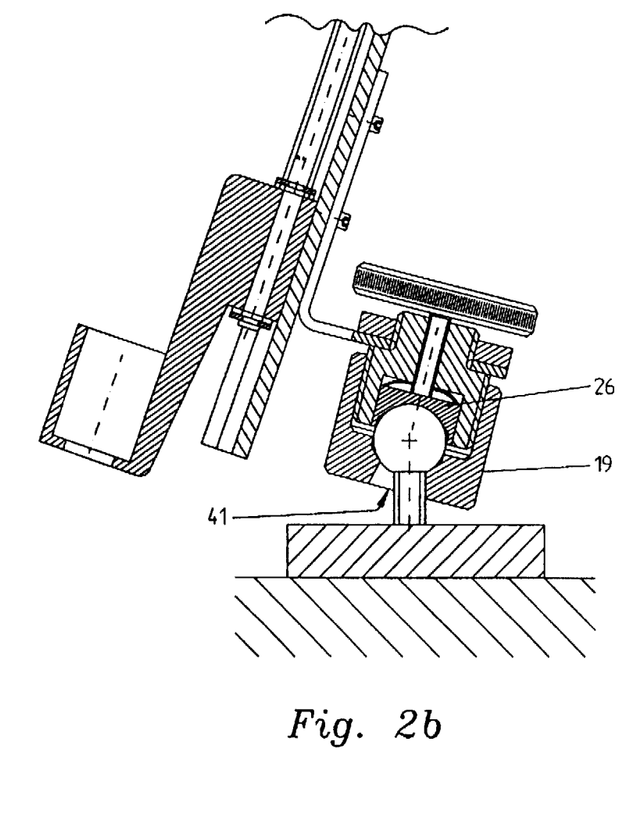
FIG. 2b shows a cutaway of the clamped ball-and-socket joint of the positioning system according to the invention.

FIGS. 2a and 2b illustrate how clampable ball-and-socket joint 3 works. In FIG. 2a, the ball-and-socket joint 3 is unclamped. The three dimensional position of the three rotational axes 22, 23, 24 is held by spring pretension. In FIG. 2b, the linear axis is swung to the side and the ball-and-socket joint is clamped. The instantaneous position is secured by a pretensioning spring force and also by the axial force of clamp screw 20 on the ball surface.

Through conical opening 41 on the bottom of housing 19 of ball-and-socket joint 3, column 25 leads to base 4. Ball 21, column 25 and base 4, thus, form a rigid unit. Clamp screw 20 acts on the outer surface of ball 21 via movable ball seat 26. FIG. 2b shows how ball 21 is securely clamped when clamp screw 20 is tightened between the contact surfaces of ball seat 26 and the corresponding opposite surfaces of housing 19. The selected three-dimensional position in the three rotational degrees of freedom 22, 23, 24 is thus securely fixed. When loosening the clamp screw 20 shown in FIG. 2a, conversely, the unclamped ball will not allow tilting of the entire positioning system, but the selected position will continue to be maintained by friction. This is done by axially prestressed spring element 42 acting on ball seat 26, even after loosening of clamp screw 20, and with the correspondingly preselected prestress securing the three-dimensional position of the ball-andsocket joint by frictional engagement, but still allowing manual movements of the entire system.

The entire linear axis mechanism 2, together with inserted instrument 12 and housing 19 of ball-and-socket joint 3, thus can be swung around the center of ball 21 in all three of the rotational degrees of freedom 22, 23, 24, the friction of prestressed spring element 42 on the ball surface, even with clamp screw 20 loosened, preventing tilting of the system.

The primary dimensions of the entire system are, for example, an overall height above the surface of the body of roughly 100 mm and a total width of 40 mm.

In FIG. 3, a combination of the described positioning system 1 and a surgical retractor 27 for intraoperative use is shown as a first preferred embodiment. In this case, positioning system 1, together with linear axis mechanism 2 and the clampable ball-and-socket joint 3, is joined with its base 4 securely to any retractor 27. After inserting retractor 27 into body opening 28 which is made, for example, by a surgical tissue incision, and subsequent spreading of retractor 27 in body opening 28, retractor 27, together with the positioning system 1 attached to it, is securely joined to the body.

By manipulating the four axes of movement 15, 22, 23 and 24, thus, intraoperatively, the free active end 14 of any instrument 12 which is clamped securely into the positioning system can be precisely guided to any destination 16 located in body 17. If positioning is to be done on structures which are no longer visible with the naked eye, the position of the free active end in the body opening can be visually monitored, for example, by a microscope. Here, positioning system 1 is located on retractor 27 such that optical axis 30 of the microscope or naked eye 29 is not hidden by positioning system 1 itself or its parts.

Preferred body openings 28 in which positioning system 1 can be used intraoperatively with a suitable retractor 27 are, for example, incisions in soft tissues, the external auditory canal, the mastoid antrum or openings in the skull bone for neurosurgery.

Accordingly, preferred destinations 16 on the body, at which free active end 14 of positionable instrument 12 is to be pointed are among others, microsurgical structures on or in the spinal column, within the skull, in the external auditory canal, on the ear drum, in the opened cavities of the middle ear (malleus, incus, stapes), on the bone wall between the middle and inner ear (promontorium), on the liquid-filled inner ear, on the auditory nerve, in the vestibular organ, or in the eye cavity.

Suitable instruments 12 for use in positioning system 1 in conjunction with suitable retractors 27 are, among others, piezoelectric hearing aid transducers for electromechanical vibrational stimulation of the auditory ossicle chain, exciter coils for electromagnetic stimulation of permanent magnets fixed to the chain, optical fibers for guiding surgical laser light (for example, for cutting, drilling, coagulating or obliterating tissue or bone structures), optical fibers for guiding measurement laser light (laser doppler vibrometry), a flexible miniature endoscope for inspection in the entire skull area, probe microphone, and small noise sources for intraoperative audiometry (hearing threshold determination, measurement of otoacoustic emissions) and electrodes for electrocochleographic derivation of body potentials, such as the sum action potential (SAP) or microphone potential (MP).

Figure 4:
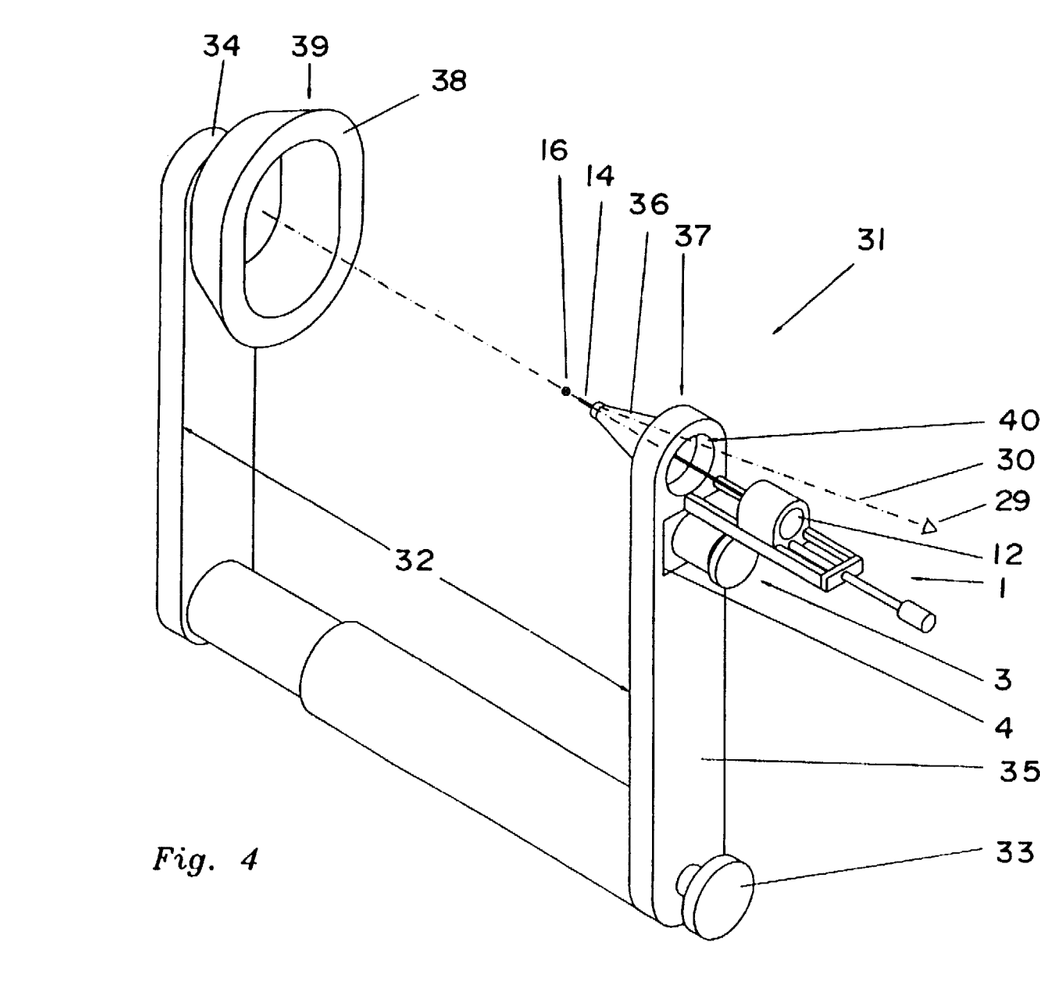
FIG. 4 shows a schematic overall view of the positioning system combined with a head support for noninvasive, diagnostic or therapeutic use according to the invention.

As a second preferred embodiment, FIG. 4 shows a combination of positioning system 1 and a head support 31 for noninvasive, diagnostic or therapeutic use of instruments anchored to the skull. In the version shown here, the positioning system 1 is securely joined with its base 4 to a head support 31. Opening width 32 of the head support 31 is, preferably, roughly 200 mm, and width 32 can be set, optionally and without play, via a knob 33 and an interior threaded drive by moving two receiving arms 34 and 35 towards (closing) or away (opening) from one another. Knob 33 for adjustment of opening width 32, in this case, can be operated either by the wearer of head support 31 himself/herself or by a qualified specialist (physician, nurse, assistant) in order to attach head support 31 to the head of the patient by clamping on both sides. Positioning system 1 with its base 4 is attached securely to one of two receiving arms 35. This side is called the working side 37 of the head support.

A conical retaining element 36 can be made, for example, like an ear speculum which, when necessary, can be placed on gimbals in receiving arm 35 to equalize small spatial angles. It is inserted into the external auditory canal of the wearer (patient) with visual monitoring, if necessary, with the aid of a microscope. Conical retaining element 36, moreover, has a conical inside opening 40 which provides space for the free, active end 14 of the instrument 12 clamped in positioning system 1 and also for visual control.

On the receiving arm 34 on the opposite side 39 of head support 31, selectively, a second conical support, similar to support 36, or an earmuff element 38 in the form of a half shell, is attached. The second conical support or earmuff element 38 is, respectively, inserted into the auditory canal or placed over the outer part of the opposite ear.

When earmuff element 38 is used, as is shown in FIG. 4, some of the pretensioning force is transferred over a large area to the skull bone area which surrounds the outer ear by reducing the opening width 32. This prevents compressive forces from being applied at points and the associated undesirable feeling of pressure associated with it, and the force applied for support is distributed over a large area of skin.

After inserting conical retaining element 36 of working side 37 into the outer auditory canal and the subsequent placement of the earmuff element 38 on the outer ear of the opposite side 39, by carefully reducing opening width 32 of head support 31, the two retaining elements, i.e., retaining element 36 and earmuff element 38, can be caused to approach one another until the entire head support 31 is clamped on the skull of the patient. By deforming earmuff element 38 and by blocking conical retaining element 36 in the outer auditory canal, a secure filling of the entire head support 31 on the skull of the patient is ensured. By means of conical inside hole 40 in conical retaining element 36, after clamping head support 31 on the skull of the patient, the free, active end 14 of instrument 12, attached in positioning system 1, can be positioned without play so as to prevent relative movements between the skull and target points 16 on the skull. The set position of the positioning system can be fixed via the already described clamping means of the positioning system (see FIG. 2a and FIG. 2b).

One preferred body opening 28 in which positioning system 1 can be used noninvasively or with minimal invasiveness, using a suitable head support 31, is the external auditory canal of a human.

Accordingly, preferred destinations 16 on the body, at which the free, active end 14 of the positionable instrument 12 is to be noninvasively pointed, among others, are microsurgical structures in the auditory canal itself, on or in the eardrum or the manubrium which is fused directly to the inside of the eardrum, and which represents the outermost point of the auditory ossicle chain which can be reached noninvasively through the auditory canal.

In local, minimally invasive use of this second embodiment, after opening the eardrum, moreover, positioning of the instrument relative to the anatomical structures of the air filled middle ear (malleus, incus, stapes) or the bony wall between the middle and inner ear (promontorium) is possible.

For noninvasive use of positioning system 1 in conjunction with suitable head supports 31, all instruments described with reference to the first preferred embodiment are equally applicable.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as are encompassed by the scope of the appended claims.

We claim:

1. Fixable positioning system for secure, play-free fastening of a surgical, therapeutic or diagnostic instrument relative to a human body, comprising:
   a holder having a head support configured for bilateral fixing directly to a skull in ear areas thereof;
   a base attached to the holder so as to be fully supported thereon;
   a linear axis mechanism having a linear guide and a threaded spindle extending parallel to said linear guide, said linear guide having an internally threaded member attached thereto, the threaded spindle being in threaded engagement with the internally threaded members to form a threaded drive and being axially movable relative to said linear guide by manual rotation of said spindle;
   a receiving device for receiving said instrument, said receiving device being connected to said threaded spindle for axial movement therewith and being guided by said linear guide for linear movement along said linear guide; and
   a ball-and-socket joint which is manually movable in three rotational degrees of freedom and which is fixable via a clamp mechanism, said ball-and-socket joint being connected between the base and the linear guide of the linear axis mechanism.

2. Positioning system according to claim 1, wherein the linear axis mechanism has a self-locking construction.

3. Positioning system according to claim 1, wherein said receiving device is configured for receiving an instrument which is one of an actuator and a sensor instrument.

4. Positioning system according to claim 1, wherein the positioning system, as a result of degrees of freedom of the linear axis mechanism and of the ball-and-socket joint, in combination, provides a means for moving the instrument in one axial and three rotational degrees of freedom.

5. Positioning system according to claim 1, further comprising a rotary knob for axial and self-locking movement of the spindle mechanism by manual turning of the rotary knob.

6. Positioning system according to claim 1, further comprising a clamp screw for fixing the ball-and-socket joint in a current position relative to all three rotational degrees of freedom.

7. Positioning system according to claim 1, wherein the ball-and-socket joint is provided with means for securing thereof in a current position by creating sufficient frictional holding forces when said clamp mechanism is in a released condition.

8. Positioning system according to claim 1, wherein the construction and the geometrical dimensions of the positioning system provide an unobstructed line of sight for an operator with respect to at least a free, active end of the instrument, as well as a working area and a destination in a human body.

9. Positioning system according to claim 1, wherein the receiving device is configured for receiving an instrument which is an electromechanical actuator for vibrational stimulation of an auditory ossicle chain or eardrum of a human body.

10. Positioning system according to claim 1, wherein the holder has a retractor.

11. Positioning system according to claim 10, wherein the retractor comprises a means for anchoring the positioning system in the external auditory canal or in the opened mastoid antrum.

12. Positioning system according to claim 1, wherein the head support, on a working side thereof, is provided with a funnel-shaped retaining element having means for fixing the retaining element in the auditory canal of a human body, said funnel-shape retaing element being adapted to guide a free, active end of instrument through the funnel-shaped retaining element to a destination in the human body.

13. Positioning system according to claim 12, wherein the retaining element forms a first bearing surface for the head support on said working side; and wherein the head support, on a side opposite said working side thereof, has a soft molded part which surrounds an outer ear and which forms a second bearing surface for the head support.

14. Positioning system according to claim 13, wherein the molded part is made as a one-sided headset or noise protection.

15. Positioning system according to claim 1, further comprising a threaded drive and a rotary knob for continuous and self-locking adjustment of a clamping width of the head support between a working side and a side opposite to said working side.

16. Positioning system according to claim 1, wherein the receiving device is configured for receiving an instrument which is a diagnostic, therapeutic or surgical sensor.

17. Positioning system according to claim 1, wherein the receiving device is configured for receiving an instrument which is a diagnostic, therapeutic or surgical actuator.

18. Positioning system according to claim 1, wherein the receiving device is configured for receiving an instrument which is an electromechanical actuator for coupling to the hammer, anvil, stapes, or eardrum of the human body.

* * * * *